(12) United States Patent
Denker et al.

(10) Patent No.: US 8,366,628 B2
(45) Date of Patent: Feb. 5, 2013

(54) SIGNAL SENSING IN AN IMPLANTED APPARATUS WITH AN INTERNAL REFERENCE

(75) Inventors: Stephen T. Denker, Mequon, WI (US); Cherik Bulkes, Sussex, WI (US)

(73) Assignee: Kenergy, Inc., Mequon, WI (US)

( * ) Notice: Subject to any disclaimer, the term of this patent is extended or adjusted under 35 U.S.C. 154(b) by 154 days.

(21) Appl. No.: 12/832,098

(22) Filed: Jul. 8, 2010

(65) Prior Publication Data

US 2010/0274114 A1 Oct. 28, 2010

Related U.S. Application Data

(63) Continuation-in-part of application No. 11/759,489, filed on Jun. 7, 2007, now abandoned, and a continuation-in-part of application No. 11/959,952, filed on Dec. 19, 2007, now abandoned.

(51) Int. Cl.
*A61B 5/02* (2006.01)
(52) U.S. Cl. ......... 600/508; 600/509; 600/510; 600/523
(58) Field of Classification Search .......... 600/508–510, 600/523
See application file for complete search history.

(56) References Cited

U.S. PATENT DOCUMENTS

| | | | |
|---|---|---|---|
| 4,192,318 A | 3/1980 | Dam et al. | |
| 4,237,897 A | 12/1980 | Beane et al. | |
| 4,513,752 A | 4/1985 | Weyant | |
| 4,596,252 A | 6/1986 | Nelson | |
| 4,803,997 A | 2/1989 | Bowman | |
| 4,972,835 A | 11/1990 | Carroll et al. | |
| 5,217,010 A | 6/1993 | Tsitlik et al. | |
| 5,317,162 A | 5/1994 | Pinsky et al. | 250/461.2 |
| 5,484,444 A | 1/1996 | Braunschweiler et al. | |
| 6,019,777 A | 2/2000 | MacKenzie | |
| 6,020,783 A | 2/2000 | Coppola | 327/556 |
| 6,133,787 A * | 10/2000 | Yerkovich et al. | 330/68 |
| 6,258,117 B1 | 7/2001 | Camrud et al. | |
| 6,577,893 B1 * | 6/2003 | Besson et al. | 600/509 |
| 6,611,705 B2 * | 8/2003 | Hopman et al. | 600/509 |
| 6,943,720 B2 | 9/2005 | Nakamori et al. | 341/156 |
| 6,950,694 B2 * | 9/2005 | Yonce | 600/509 |
| 7,003,350 B2 | 2/2006 | Denker et al. | |
| 7,395,109 B2 * | 7/2008 | Drakulic | 600/509 |
| 7,453,354 B2 * | 11/2008 | Reiter et al. | 340/539.12 |
| 7,672,714 B2 * | 3/2010 | Kuo et al. | 600/509 |
| 7,780,607 B2 * | 8/2010 | Ferek-Petric | 600/508 |
| 7,818,050 B2 * | 10/2010 | Rapoport et al. | 600/511 |
| 2002/0026224 A1 | 2/2002 | Thompson et al. | |
| 2002/0049477 A1 | 4/2002 | Zhang et al. | |
| 2002/0128546 A1 | 9/2002 | Silver | |
| 2003/0130683 A1 | 7/2003 | Andreas et al. | |
| 2003/0135258 A1 | 7/2003 | Andreas et al. | |
| 2003/0135266 A1 | 7/2003 | Chew et al. | |
| 2004/0093061 A1 | 5/2004 | Acosta et al. | |
| 2004/0098081 A1 | 5/2004 | Landreville et al. | |
| 2004/0186551 A1 | 9/2004 | Kao et al. | |
| 2004/0215312 A1 | 10/2004 | Andreas | |

(Continued)

*Primary Examiner* — Kenneth B. Wells
(74) *Attorney, Agent, or Firm* — Quarles & Brady LLP; George E. Haas

(57) ABSTRACT

An implantable apparatus for sensing biological signals from an animal includes at least two electrodes disposed at locations to sense the biological signals. The electrode locations may be internal or external to the animal. Insulated conductors couple the electrodes via a passive network of filters to an instrumentation amplifier that has an internal voltage reference. Thus a sensed biological signal is filtered and amplified to provide an amplified differential signal. A signal analysis module processes amplified differential signal to determine at least one physiological parameter of the animal. The signal analysis module may include a first derivative zero detector for signal transition detection and feature detection and analysis. The apparatus may also comprise a signal presentation module to display amplified signals and physiological parameters associated with those signals.

20 Claims, 4 Drawing Sheets

U.S. PATENT DOCUMENTS

| | | |
|---|---|---|
| 2004/0215331 A1 | 10/2004 | Chew et al. |
| 2004/0249434 A1 | 12/2004 | Andreas et al. |
| 2004/0249435 A1 | 12/2004 | Andreas et al. |
| 2004/0260380 A1 | 12/2004 | Marco et al. |
| 2005/0010276 A1 | 1/2005 | Acosta et al. |
| 2005/0049673 A1 | 3/2005 | Andreas et al. |
| 2005/0083145 A1 | 4/2005 | Ravi et al. .................... 331/186 |
| 2005/0110550 A1 | 5/2005 | Shi et al. ....................... 327/307 |
| 2005/0261596 A1 | 11/2005 | Smith |
| 2005/0264435 A1 | 12/2005 | Bicking ........................... 341/15 |
| 2006/0241732 A1 | 10/2006 | Denker et al. |
| 2006/0244479 A1 | 11/2006 | Major ............................ 326/29 |
| 2007/0057719 A1 | 3/2007 | Kitano .......................... 327/552 |

\* cited by examiner

SIGNAL SENSING IN AN IMPLANTED APPARATUS WITH AN INTERNAL REFERENCE

CROSS REFERENCE TO RELATED APPLICATIONS

This application is a continuation-in-part of U.S. patent application Ser. No. 11/759,489 filed on Jun. 7, 2007 now abandoned and is a continuation-in-part of U.S. patent application Ser. No. 11/959,952 filed on Dec. 19, 2007 now abandoned, the disclosures in which are incorporated herein by reference as if set forth in their entirety herein.

STATEMENT REGARDING FEDERALLY SPONSORED RESEARCH OR DEVELOPMENT

Not Applicable.

BACKGROUND OF THE INVENTION

1. Field of the Invention

The present invention relates to medical devices, which provide a mechanism to sense physiological signals from nerves and muscles in humans. Specifically, the current invention relates to sensing, processing and feature extraction of physiological signals in their pristine form while avoiding error sources arising from electrical noise, signal amplitude variations, DC drift, and filtering.

2. Description of the Related Art

Electrical Noise

In an exemplary case of electrical sensing and amplifying of physiological signals, the amplifier has competing electromagnetic signal sources that may cause deterioration of signal quality performance. Established methods use common mode rejecting amplifier designs, which reference the leads of a signal pair to a reference and a real or virtual ground. When the signals have amplitudes in the range of a few tens of mV, the performance of such solutions is good, as the operating voltage range is many orders of magnitude greater than the supplied signal. On the other hand, for biological signals encountered in electrocardiography (ECG) and electroencephalography (EEG), the traditional techniques with an external ground are not optimal as the relatively smaller magnitude of the biological signals can be easily overwhelmed by noise.

In a conventional data acquisition system, the input bandwidth must be limited to avoid aliasing. Aliasing is the result of not having sufficient data samples available to distinguish a component with frequency content F from one with n×2F. However, aliasing would become an issue only if sufficient energy is contained in higher frequencies. According to the Shannon/Nyquist theorem, the sample frequency must be at least twice the lowest frequency component contained in the signal at the lowest amplitude of the dynamic range of the system.

The frequency range for ECG signals has traditionally included the line frequencies, 50 Hz and 60 Hz. In a traditional system, with an input pair and a common ground in an office, home or industrial environment, there is likely considerable line frequency content in the input signal, at the input amplifier and/or sampling location. One solution would include a notch filter for 50 Hz and 60 Hz, or one broad band enough to filter out the band from 45-65 Hz. By Shannon/Nyquist, the notch filtering will introduce a non-linear effect from at least 22.5 Hz to 130 Hz resulting in system sensitivity reduction. Even a high Q filter will not avoid this issue. The other common line frequency for aviation and marine equipment is 400 Hz. However, this is generally high enough not to affect ECG signals. If there is no meaningful information contained in the filtered out band, there will not be any adverse issues with the filtering approach. In practical applications, that is almost never the case. Since important information is contained in those frequency bands, there is a need for a technique that includes the entire band from 10 Hz to 200 Hz so pristine biological signals can be acquired.

Another problem afflicting present-day devices relates to the rejection of amplitude modulated or burst electromagnetic fields. One source of burst line frequency noise is faulty, or poorly designed, appliances where the patient is in close proximity of or in contact with a line frequency AC powered device. The patient actually is part of a direct or induced electrical pathway to ground. In contrast, to sense detection in the presence of continuous additive line frequency interference, the operation of the sensing circuit during amplitude modulated or burst electromagnetic interference (EMI) is probably more important to patient safety. Burst line frequency noise is a potentially dangerous situation for pacemaker-dependent patients because burst noise may inhibit stimulus generation in a cardiac control device. The potential hazard of continuous line frequency noise, in comparison to burst noise, is less precarious because continuous line noise will cause the device to pace asynchronously with respect to a spontaneous cardiac rate, but the device will still support the patient.

A further problem with prior art techniques is the usage of digital or active analog filtering in the front end circuit that is directly connected to electrodes. This exposes the internal circuits to the full noise amplitude and has the risk of running out of "dynamic range." For example, if the amplifier output hits the rails (ground or supply), it is no longer linear, or amplifying. For example, given a normal signal range of 1-10 mV, a gain of 200, a noise burst of 100 mV and a 5 volt supply rail, the output amplitude of the true signal is 200 mV to 1.0 volt and the noise signal in the output is 20 volts, which is well beyond the supply rail voltage. The amplifier may simply peg at the rail, or oscillate between ground and a supply voltage level, without linear relation to the input signal.

Yet another problem with prior techniques relates to difficulty in cardiac monitoring when attempting to segregate electrical noise (EMI) from fibrillation. The QRS complex is high bandwidth (50-500 Hz), with conventional methods showing 2-60 Hz and an inability to detect the characteristic high slew rate QR complex (about 50-100 μsec for min to max–about a 10-20 mV amplitude) Standard systems require high gain (500×) to get to a reasonable 1.0 V pp signal, as the ECG amplitude is documented as a 2-10 mV signal. However, the composition at 50-500 Hz is very different. The highest amplitudes are the shortest duration, and classic low BW filtering reduces these to slower, lower amplitude. This difficulty in differentiating EMI from QRS manifests in cardiac monitoring and rhythm diagnosis both on surface ECG and internally in pacemakers and defibrillators. The potential for unnecessary shocks from implantable defibrillators makes the internal case particularly significant. Improved noise immunity is needed.

Signal Amplitude Variations, DC Drift, and Filtering and their Effects on Signal Transition Detection and Feature Extraction Medical devices often require signal processing based on signal transition detection for the purpose of feature extraction. The results of feature extraction on physiological signals may be used to discern the exact nature of the underlying physiological processes, in some cases even enabling autonomous actions by electronic instruments embedded within a human (e.g. pacemaker and/or defibrillator).

In an exemplary case, established methods use detection of signal transitions as the starting point for feature extraction, Variations in signal amplitudes, and superposition of DC drift upon the signal, may introduce significant errors into signal transition detection, thereby potentially adversely impacting the ultimate decision making resulting from feature extraction.

Transition detection has been conventionally accomplished by detecting signal zero-crossings. However, any low frequency contamination of the signal may cause the "baseline" or "the zero line" to wander, thereby compromising the accuracy of zero crossing detection. In this case, the signal may be prevented from crossing the baseline as a result of low frequency content. To address this, one solution has been to amplify the signal into a fixed amplitude limit, thereby removing the amplitude information before applying the zero crossing detection. The result is a "band limited signal" that does not contain any valid signal components above or below cutoff frequencies of a pass band. Nevertheless, a band limited signal contains low amplitude components from the stop bands, i.e. frequencies above or below the pass band, or noise. The low frequency content would still be prevalent and cause inaccuracies in signal detection. Such noise may cause erroneous detection of zero-crossings. Additionally, removing the amplitude information in this way precludes later re-production of the original signal.

Other current signal processing methodologies perform band pass filtering and compression of the signal to minimize dynamic range, and then pass the result through a signal transition detector. Signal amplitude compression tends to produce a constant amplitude signal, or at least one with minimal dynamic range. Therefore a desired detector would be amplitude independent, and thus not directly be affected by band pass filtering controlling amplitude.

In the cardiac arena, a problem with prior-art cardiac monitoring systems is difficulty differentiating between the QRS and T waves. In reality the two are quite different: QRS is high frequency, short duration, whereas T wave is low frequency, long duration. In traditional systems these sometimes appear to have similar (20.50%) levels in amplitude and appear 'rounded'. Comparison of the real signals shows no such similarity (the T wave is <10% of the QRS). Mistaking a T wave for another heart beat could produce a double heart rate, and subsequent misinterpretation for ventricular tachycardia. Current systems use a "lock out" for the T wave complex, to avoid mis-detecting it, assuming that a steady heart beat is normally available and serves to more or less 'predict' where the next beat should be. It's called a 'lock-out' feature. This difficulty in differentiating QRS from T manifests in cardiac monitoring and rhythm diagnosis both on external ECG and internally in pacemakers and defibrillators, The potential for unnecessary shocks from implantable defibrillators makes the internal case particularly significant. An improved signal transition detector would alleviate this problem.

Again related to cardiac, there exists a need to identify existing substrates (chronic substrates) in cardiac muscle which could cause serious rhythm abnormalities such as ventricular tachycardia. The prior-art demonstrates two established methods (T wave alternans and Signal averaged ECG). Both of these methods require signal averaging and amplification because of the necessary filtering of the current techniques to remove EMI. An improved signal transition detector is needed to provide a superiorly pure signal, thereby alleviating the necessity of signal averaging.

Further related to cardiac, there also exists a need to identify real time changing substrates in cardiac muscle which are electrical reflections of mechanical and ischemic (reduced blood supply) changes in the ventricular muscle. If a patient's heart failure is worsening there are going to be changes in mechanical stretch characteristics of the muscle and a high fidelity electrical signal would reflect this mechanical change, as it also would in the event of an ischemic event to the muscle. Prior-art offers no signal transition detection techniques with sufficient fidelity to perform diagnoses based on such detections. An improved signal transition detector is needed to produce signals of such fidelity.

Related to EEG, there exists a need to obtain higher fidelity, less noisy signals. The prior art uses single ended detection (—i.e. the micro-Volt signals are carried in single ended with a 'common' usually clipped to an earlobe). Muscle signals are about 50× greater in amplitude than neuronal signals (muscle=10 mV, neuron=0.2 mV). An EEG needs to be devoid of low frequency disturbances, although group wave patterns are from 2-40 Hz. Detail is visible up to several hundreds of hertz, but not currently cataloged due to noise contamination. Noise is tremendous and any muscle noise dominates (eyebrows, eyes, facial, jaw, swallowing). Use of the groundless amplification and first derivative zero detection techniques of this disclosure would greatly enhance EEG signal fidelity and usefulness.

In view of all of the foregoing discussion, there is a need for a system that can amplify biological signals from muscles and/or nerves without concomitantly amplifying the noise. There is also a need for a signal transition detector that is not subject to DC drift in the signal, is not subject to signal amplitude variations, does not lose signals with the usual filtering processes, lends itself amenably to robust feature detection, and allows for reproduction of the original signal but without the DC component.

SUMMARY OF THE INVENTION

An amplifier with an internal voltage reference, and powered by an energy source without being connected to mains or an isolation transformer of medical equipment, is introduced. Such an amplifier is applicable to processing signals from both internally implanted, and externally applied, electrode pairs on an animal.

A signal transition detector based on first derivative zero detection is also introduced. Since for every signal zero crossing there is a peak signal transition, either from negative to positive or vice versa, counting signal peak transitions is similar to counting signal zero crossings. Unlike zero crossings, however, peak transitions in general are detected without need for a specific threshold that may change with average signal. Moreover, detection of peak transitions may allow computation of time difference between signal transitions, which essentially carry the frequency information. The desired detector can have an implied response limit, but it can be chosen to allow processing of a full bandwidth for the application. Such a transition detector is applicable to processing signals from both internally implanted, and externally applied, electrode pairs on an animal.

In accordance with one aspect, an apparatus for sensing biological signals from an animal is provided. The apparatus can include at least one set of electrodes that is configured to be implanted in the animal and disposed at a first set of locations to sense biological signals from the first set of locations, a set of insulated conductors connected to the at least one set of electrodes, the set of insulated conductors formed in a configuration adapted to be substantially immune to electromagnetic interference, a network of filters connected to the set of insulated conductors, the network of filters configured to filter the sensed biological signals, an amplifier connected to the network of filters, the amplifier including an internal voltage reference and the amplifier configured to amplify the filtered biological signals to provide an amplified differential signal, an energy source powering at least the amplifier, the energy source configured to be substantially free of an externally grounded energy supply external to the animal, and a signal analysis module configured to receive the amplified differential signal and to analyze the amplified differential signal to determine at least one physiological parameter. The signal analysis module may include a mechanism to identity signal transitions by first derivative zero detection. Detection of these zeroes provides a signal transition detector that is not subject to DC drift in the signal, is not subject to signal amplitude variations, does not lose signals with the usual filtering processes, that lends itself more amenably to robust feature detection, and that allows for reproduction of the original signal but without the DC component.

In accordance with another aspect of the invention, an implanted apparatus for sensing biological signals from an animal is provided. The apparatus can include at least one implanted electrode pair disposed at a first set of locations to sense biological signals. Each electrode pair can be connected to a pair of insulated conductors that are in turn connected to an instrumentation amplifier via a passive network of filters. The insulated conductors can be configured to avoid picking up of EMI noise. The amplifier can amplify the filtered biological signal from each of the electrode pairs to provide an amplified differential signal. The amplifier can have an internal voltage reference. Additionally, an energy source can power the apparatus without being connected to mains or an isolation transformer of medical equipment. A signal analysis module can analyze amplified differential signals to obtain at least one physiological parameter. The signal analysis module may include a mechanism to identity signal transitions by first derivative zero detection. Detection of these zeroes provides a signal transition detector that is not subject to DC drift in the signal, is not subject to signal amplitude variations, does not lose signals with the usual filtering processes, that lends itself more amenably to robust feature detection, and that allows for reproduction of the original signal but without the DC component.

The apparatus may also include a signal presentation module to display amplified signals and physiological parameters associated with the signal. The energy source may be a battery, an infrared source or a radio frequency source. The electrodes may be located inside a blood vessel, extravascular or transvascular and sense signals from various tissue locations.

In accordance with another aspect of the invention, an external apparatus for sensing biological signals from an animal is provided. The apparatus can include at least one electrode pair externally affixed to a first set of locations to the outside surface of an animal to sense biological signals. The purpose of such external signal collection may be in the cardiac arena for one or more of: cardiac monitoring and rhythm diagnosis; identification of existing substrates (chronic substrates) in cardiac muscle which could cause serious rhythm abnormalities; identification of real time changing substrates in cardiac muscle; and/or for other purposes in cardiac medicine. The purpose of the external signal collection may also be in the EEG arena, where there exists a great need to obtain higher fidelity, less noisy signals.

Each electrode pair can be connected to a pair of insulated conductors that are in turn connected to an instrumentation amplifier via a passive network of filters. The insulated conductors can be configured to avoid picking up of EMI noise. The amplifier can amplify the filtered biological signal from each of the electrode pairs to provide an amplified differential signal. The amplifier can have an internal voltage reference. Additionally, an energy source can power the apparatus without being connected to mains or an isolation transformer of medical equipment. A signal analysis module can analyze amplified differential signals to obtain at least one physiological parameter. The signal analysis module may include a mechanism to identity signal transitions by first derivative zero detection. Detection of these zeroes provides a signal transition detector that is not subject to DC drift in the signal, is not subject to signal amplitude variations, does not lose signals with the usual filtering processes, that lends itself more amenably to robust feature detection, and that allows for reproduction of the original signal but without the DC component.

Embodiments of the present invention can provide for the elimination of ground and associated noise sources by passive component and instrumentation amplifier design, elimination of DC and very low frequency noises by a high pass filter, elimination of common mode noise by a low pass filter over 500 Hz and a noise filter over 1 kHz. There can be no need for line frequency filtering with the elimination of traditional ground. Another aspect of the invention is the use passive filtering at the front end, before any active components are involved. Additionally, the conductors connecting to the electrodes can be paired to avoid the formation of EMI pickup loops. Another aspect of the invention is incorporation of first derivative zero detection, which eliminates prior difficulty with feature extraction in the presence of signal amplitude variations and with the usual filtering processes, and that allows for reproduction of the original signal but without the DC component.

DETAILED DESCRIPTION OF THE INVENTION

The present invention is described in both the implanted and externally applied contexts. While the implanted context may be described as in a vein or artery of the heart for cardiac pacing, the present apparatus may also be employed to sense signals from muscles and/or nerves in other areas of the human body. In addition to cardiac applications, the sensing apparatus can provide brain signal sensing, for treatment of Parkinson's seizures. Similarly, while the external context is described in the cardiac and EEG arenas, the present apparatus may also be applicable to external sensing of other human body muscle and nerve signals.

An aspect of embodiments of the invention is the use of a plurality of electrode pairs disposed at a first set of location for the signal sensing. It should be understood that each electrode pair in close proximity or farther apart is included in the set. Further, if more electrode pairs are involved, the term set should encompass all such paired locations as well. In the subsequent description, signal sensing and amplification is described at only one electrode pair for the sake of convenience and it should be understood without loss in generality, that the present invention can be configured to sense from a plurality of locations.

A signal amplifier and associated electronics that do not require an external ground is described. The signal amplifier with an internal ground will only see common mode signals especially when the signal pair is either a coaxial, ribbon or twisted pair.

Figure 1:
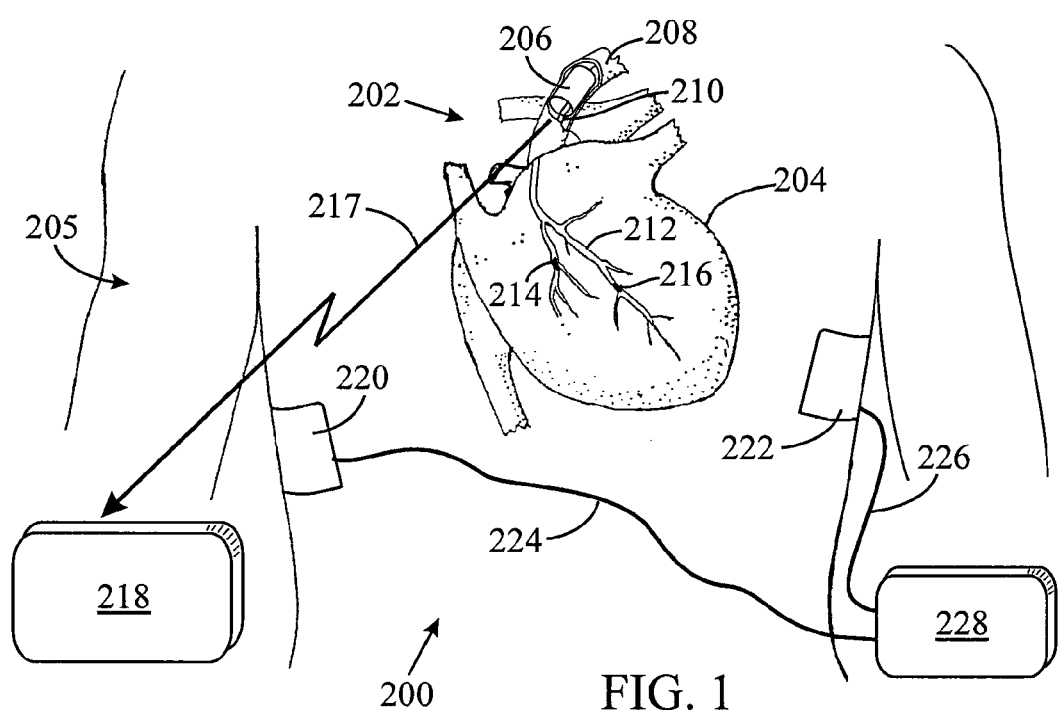
FIG. 1 depicts a cardiac signal sensing system attached to a medical patient.

Referring initially to FIG. 1, a medical apparatus 200 comprises a medical device 202 that senses electrical signals in a heart 204 of an animal 205. In one embodiment, the medical device 202 has an intravascular module 206 for sensing, filtering, and amplifying, such cardiac electrical signals. The exemplary intravascular module 206 is on a stent-like body that is secured in a vein or artery 208 in close proximity to the heart 204. One or more electrical conductors 210 extend from the intravascular module 206 through the cardiac vasculature to locations in smaller blood vessels 212 at which electrical sensing is desired. At such locations, the electrical conductors 210 are connected to a remote electrode 214 or 216 secured to the blood vessel walls. The intravascular module 206 analyzes the sensed electrical signals to determine physiological parameters of the animal, and data regarding those parameters is sent via a wireless signal 217 to equipment 218 outside the animal.

In an alternative embodiment, sensing electrodes 220 and 222 are be placed on the skin of the animal 205 and connected by electrical conductors 224 and 226 to the signal processing circuitry in an external module 228.

Both of those embodiments of the medical apparatus include a unique sensing, filtering, and amplification module that processes the sensed physiological signals from the animal.

Figure 2:
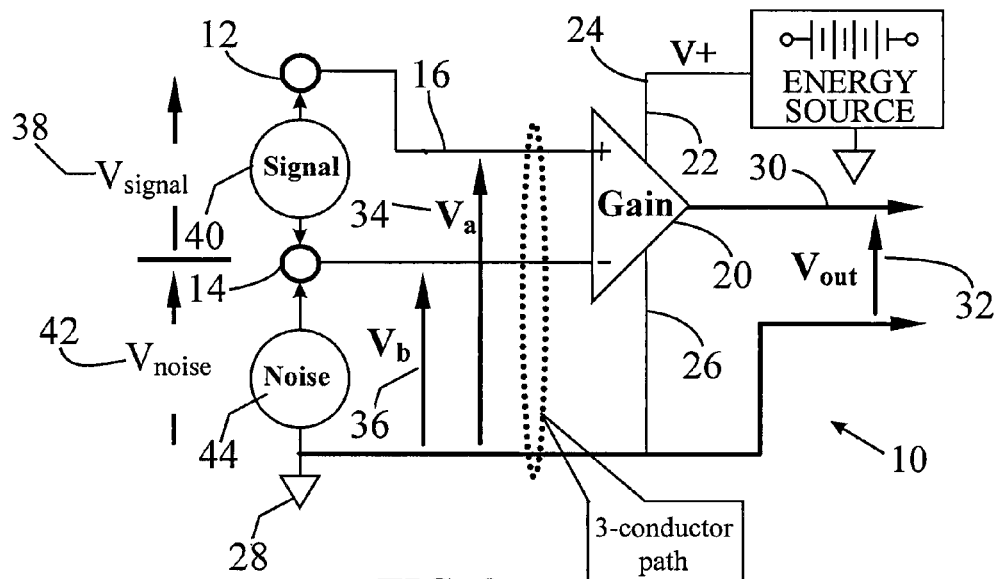
FIG. 2 is a schematic diagram of a sensing amplifier system with a three-conductor path.

FIG. 2 illustrates a three-conductor version of the sensing, filtering, and amplification module 10. This module 10 includes a pair of implantable electrodes 12 and 14 connected by a pair of insulated conductors 16 and 18 to an amplifier 20. The amplifier 20 is connected by line 22 to a positive supply line 24, is connected on line 26 to an external ground 28. The amplifier 20 produces an amplified signal at output 30. In this case, $V_{out}$ 32 is the voltage of the output signal, $V_a$ 34 and $V_b$ 36 are the voltages sensed by electrodes 12 and 14, $V_{signal}$ 38 is the voltage of signal 40, $V_{noise}$ 42 is the voltage of noise 44, and Gain is the voltage gain of the instrumentation amplifier 20. Now, $V_{out}=Gain(V_a-V_b)$; where $V_a=V_{signal}+V_{noise}$ and $V_b=V_{noise}$. In the difference mode, we can subtract out the $V_{noise}$, with "$Gain(V_{noise}-V_{noise})=0$", leaving $V_{out}=Gain(V_a-V_b)$.

Figure 3:
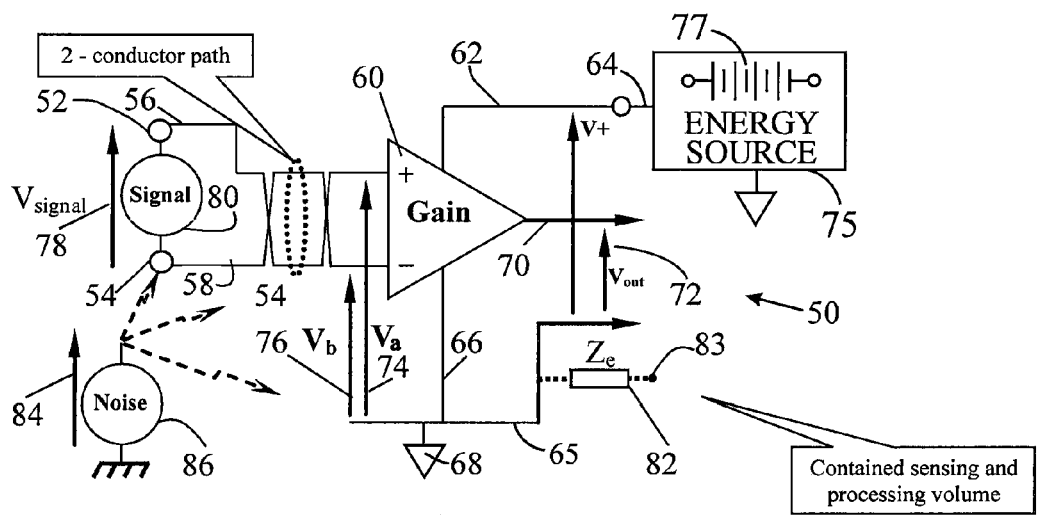
FIG. 3 is a schematic diagram of a sensing amplifier system with a two-conductor path.

EMI Noise Mitigation:

If the main signal leads (providing $V_a$ and $V_b$) are contained within a space or volume with noise sources external to that volume, the external ground reference may be removed with a concomitant performance improvement of the sensing, filtering, and amplification module 50 in FIG. 3.

In the implanted system, the body is the containing volume which encloses the main signal leads. In the external system, the electrodes are applied to the outside of the animal, and the main signal leads are shielded and run to an interface box containing the amplifier 60. The shield of the main signal leads, and the interface box, together comprise the containing volume.

System 50 includes a pair of implantable or externally attached electrodes 52, 54 connected on conductors 56, 58 to amplifier 60. Amplifier 60 is connected via line 62 to a positive supply line 64 from an energy source 75, is connected by line 66 to internal ground 68, and has an output 70. The energy source 75 may comprise an implanted battery 77 which may be charged wirelessly from an infrared light source or from a radio frequency signal source. By removing the external reference or ground, the signal lines may be exposed to common mode noise. However, without a path to reference this noise, a common mode circuit cannot be formed. This results in the original signals being presented to the amplifier. By arranging the two signal conductors 56, 58 in a paired fashion, it can be ensured that input conductor impedance for the signal amplifier 60 is equal for both the leads with equal noise exposure.

$V_{out}$ 72 is the voltage of the output signal, $V_a$ 74 and $V_b$ 76 are the voltages sensed by electrode pair 52, 54, $V_{signal}$ 78 is the voltage of signal 80, and Gain is the voltage gain of the instrumentation amplifier 60. In this case, $V_{out}=Gain(V_a-V_b)$, where $V_a-V_b=V_{signal}$; and $V_{out}=Gain(V_{signal})$.

In FIG. 3, Ze 82 is a virtual component between internal ground 68 and an enclosure 83 containing system 50. Ze 82 represents the impedance to the enclosing volume. When the enclosing volume has low impedance to the noise generator it will form an electrostatic shield, whose effectiveness increases proportionally to the conductivity of that environment.

There are other methods of mitigating electromagnetic interference. One of the methods include running wires in close proximity to each other, for example, 1.0 mm spacing or less, relative to the wavelength of the EMI field, e.g., 750 km for an EMI field of 400 Hz (worst case for 50/60/400 hz), from which immunity is needed. The insulated conductors 56 and 58 extend in parallel less than 3.0 mm apart.

Noise voltage 84 of noise 86 can still be injected within each individual conductor and present an unbalanced noise component to the amplifier 60 where it will be amplified and spoil the original signal. Depending on location and application, the contributions of unbalanced noise must be considered before choosing this method as described next.

Groundless Signal Amplifier/Detector:

There are a few considerations in a practical implementation of the previous circuit. First, there are DC considerations. Second, there is an internal reference consideration. Third, there are filtering considerations. In the following, each of these is described in detail.

Figure 4:
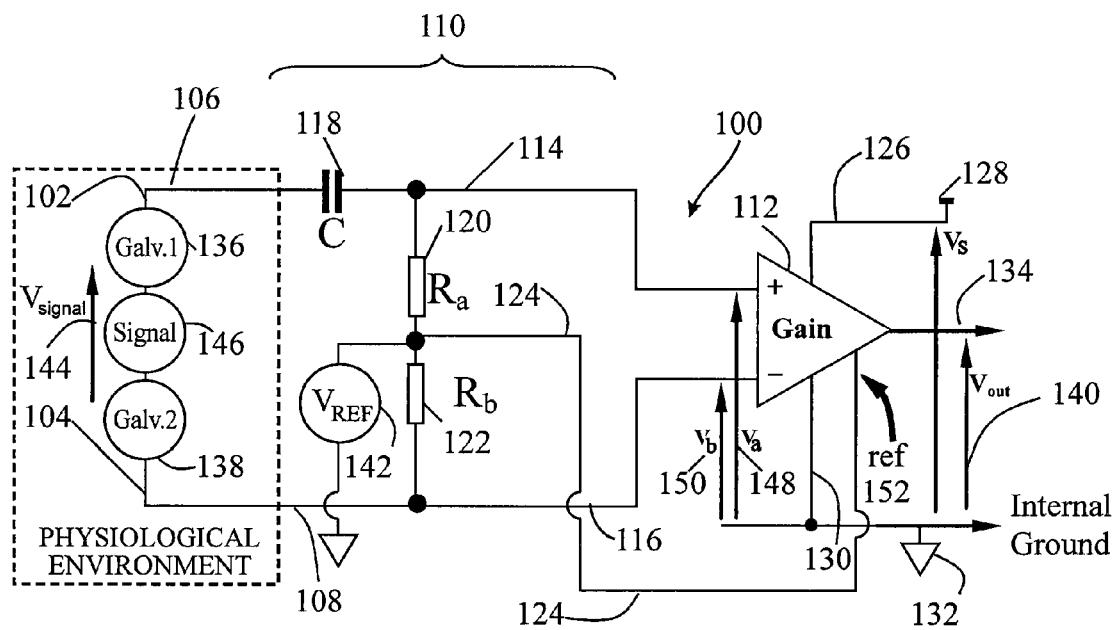
FIG. 4 is a schematic diagram of a sensing amplifier with an internal reference and a high pass filter to reject DC and low frequencies.

1. DC Considerations:

FIG. 4 illustrates components for the DC considerations. Another sensing, filtering, and amplification module 100 includes a pair of implantable electrodes 102, 104 connected on lines 106, 108 to filter network 110, which is connected to amplifier 112 by lines 114, 116. Line 116 is connected to line 108, which means that lines 116 and 108 can be considered a single line. Filter network 110 includes a capacitor 118 having a capacitance C, a resistor 120 having a resistance Ra, and a resistor 122 having a resistance Rb. Capacitor 118 is connected between lines 106 and 114. Resistor 120 is connected between lines 114 and a line 124; and resistor 122 is connected between line 124 and line 116. Amplifier is connected on line 126 to a positive supply line 128 from an energy source, is connected on line 130 to internal ground 132, and has an output 134.

At the interface between electrode and tissue, a galvanic system is formed with a DC potential. If there is complete symmetry in this circuit from electrode-1 to electrode-2, then the sum of all the contact potentials will cancel. However, if the materials used are dissimilar, the electrode/tissue and or the electrode/blood interface will yield potentially different galvanic generators that do not cancel. In this case, the input amplifier is presented with the source voltage of interest along with the galvanic voltage difference. This galvanic component is relatively static, but it could potentially be modulated with body or organ movement, as the electrode may wander between touching the vessel wall and the blood pool thereby presenting a varying "DC" voltage. The variance over time is expected to be synchronous with the movement, and thus in the sub 2 Hz range, if respiratory and cardiac movements are included. Another DC issue stems from the amplifier itself, which will require a DC current bias into or out of the input terminals. In MOSFET amplifiers, this "bias current" is very small, but doubles with every ten degree Celsius (10° C.) in temperature rise. Also, this current can have an offset, leaving a differential current that can spoil the balance of a high impedance circuit. This problem can be substantially alleviated by providing a form of AC coupling with the electrodes, and a DC current path for the bias currents.

The AC coupling performs two functions. The first function is DC decoupling from the galvanic voltages, Galv.1 136 and Galv.2 138, and the second function is to form a high pass filter with a corner frequency of $F_{HP}=1/2\pi RC$, where $R=Ra+Rb$.

The bias and offset currents are in the order of $10^{-9}$ to $10^{-8}$ A, and with path resistances of e.g. 100 kOhm, still yield 0.1 to 1.0 mV. Since source voltages are in order of 0.5-10 mV, these bias and offset voltages are not negligible. Therefore, in this embodiment, the amplifier specification selection should be such that these currents are low enough to allow for reasonably high input resistance values in the order of 100 kOhm or better for Ra and Rb (FIG. 3).

Careful selection of Ra and Rb will yield an acceptable low bias current offset voltage component ($V_{offset}=I_{offset} \times Ra$, where Ra=Rb), and a proper $F_{HP}$ (high pass filter frequency). The traditional corner frequency range for $F_{HP}$ is in the order of 0.5 Hz to 2.0 Hz, but other values can be selected depending on spectral regions of interest.

A natural feature that helps our proposed implementation is the relatively low impedance of the tissues involved, typically 300 to 120 Ohm between, for example, 5 mm spaced apart electrodes. Thus, in order to create a net 1 mV across such an impedance, energy density of 0.4 mW/m would be needed with the energy contained from 0-1 kHz.

2. Reference Considerations

In order to incorporate a floating AC coupled signal, such as the one shown in FIG. 3, it is desirable to provide a reference point. If the signal is expected to be symmetrical, a $V_{ref}=Vs/2$ can be selected, thus allowing $V_{out}$ to swing between ground and $V_s$, with a rest point at $V_{ref}$, where $V_{out}$ is the output voltage 140, $V_{ref}$ is the reference voltage 142, and Vs is the signal voltage 144 of signal 146. This reference input is provided to the output stage of the amplifier 112. Commercially available instrumentation amplifiers do have a provision to receive a reference input for the amplifier output stage. The original input signal can now be presented at the output as: $V_{out}=V_{signal} \times Gain \times F$, where F is a high pass filter function.

3. Filtering Considerations

If there is no meaningful information contained in the filtered out band, there will not be any adverse issues with the filtering approach. In practical applications, that is, however, rarely the case. Since important information is contained in those frequency bands, an embodiment is tailored to include the entire band from 10 Hz to 250 Hz. For robustness reasons even a wider range of frequencies (e.g., 2 Hz-500 Hz) can be used. With this consideration, the fast rise time of the sinus node signals containing high frequency content in the 100-250 Hz range can be easily accommodated in their pristine form. Additionally, by including these frequency components, the natural physiological signals can be easily distinguished from background signals, such as noise, voluntary and involuntary muscle movement, etc.

Figure 5:
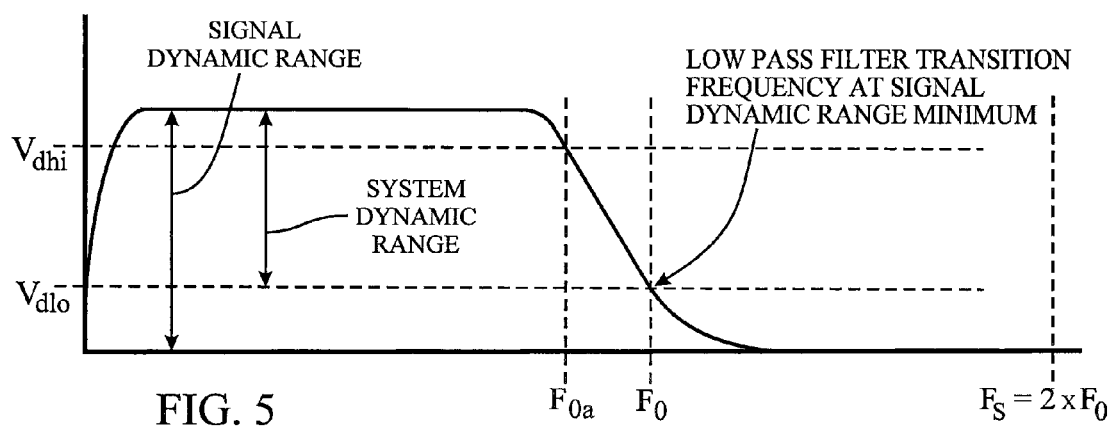
FIG. 5 shows the frequency response of band pass filtering employed by an embodiment of the invention.

FIG. 5 shows the frequency response of the band pass filtering used in embodiments of the invention. The voltages Vdhi and Vdlo represent the high and the low voltages determining the system dynamic range. The system dynamic range always excludes inherent system noise whereas the signal dynamic range is higher since it also includes noise components. The Vdlo is the voltage at which the signal falls below the intrinsic noise floor of a conventional system. $F_{Oa}$ is the low pass cut-off frequency and $F_O$ is the frequency at which the filter output goes below Vdlo. In theory, the sampling frequency ($F_S$) must be at least 2× the lowest frequency component contained in the signal at the lowest amplitude of the system dynamic range. This means that the filter transition band ($F_{Oa}$ to $F_O$) must be included when determining this lowest frequency. The high frequency filtering helps in AC coupling while the low frequency filtering helps in minimizing the noise components in the signal.

Figure 6:
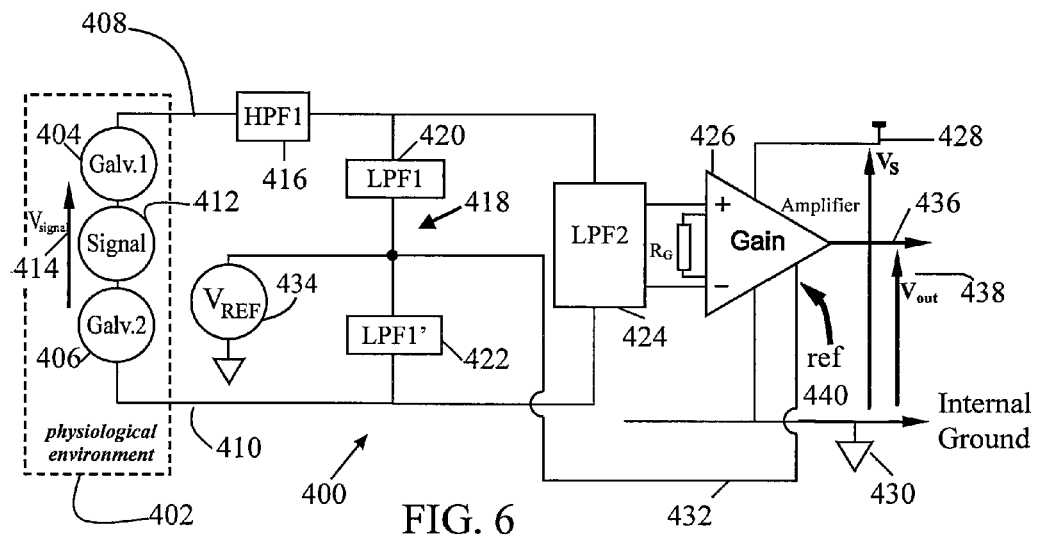
FIG. 6 is a schematic diagram of a sensing amplifier with internal reference and signal pre-filters.

FIG. 6 illustrates a system 400 according to an embodiment of the invention. A physiological environment 402 is shown to contain the galvanic voltage one 404 (Galv.1) and galvanic voltage two 406 (Galv.2) formed at the tissue electrode intersections of two electrodes 408, 410. The biological signal source that would be sensed is shown as the signal generator 412 with an associated signal voltage 414 $V_{SIGNAL}$. The source may also have associated source impedance ($Z_{SOURCE}$), which is not shown.

Between the biological environment and the signal amplifier, a network of filters, which for example can comprise at least three filters, is provided to perform various functions. The first of these filters is a high pass filter 416 to substantially block DC and low frequencies up to a predefined cut-off (e.g., 2.0 Hz). This high pass filter 416 comprises passive elements with capacitance and resistance, where resistance may be obtained by a combination of resistors, and source impedance in series. Component 416 may be a single order filter, for example. A suitable low pass filter 418 (LPF1) is configured to suppress common mode noise. Low pass filter 418 comprises assive elements 420, which can comprise capacitance C and resistance R, and their symmetrical counterparts 422 (LPF1'). A second low pass filter 424 (LPF2) is configured to reject high frequency noise signals. Low pass filter 424 filter may comprise passive elements capacitor and resistors in series. Electromagnetic broadband ambient noise from appliances and other equipment could swamp the input circuit and consume dynamic range. This needs to be filtered out. A low pass filter LPF2 with a cut-off at 1 kHz frequency can be selected since the electromagnetic noise is broad band, but its energy is rather low below 10 kHz and can be effectively filtered out.

System 400 further includes an amplifier 426 connected to the network of filters (i.e., filters 416, 418, and 424). Amplifier 426 is connected to a positive power supply 428, is connected to an internal ground 430, and receives an internal reference 432 provided by an internal reference module 434. Amplifier 426 has an output 436 having an output voltage 438.

4. Other Considerations

For ECG signals obtained by direct connection to the cardiac venous vessel wall or muscle tissue, the signal path between the two or more input electrodes should exclude any electromagnetic pickup loop, for example, by employing closely spaced wire pairs. Therefore, symmetrical layouts are favored.

Absence of a traditional ground is a significant departure from the prior art and it has obviated the need for notch filtering and other kinds of signal degrading processes. Another aspect of the invention as already mentioned is the use passive filtering at the front end, before any active components are involved. As a result, physiological signals devoid of the traditional noise are obtained.

An Integrated System

Figure 7:
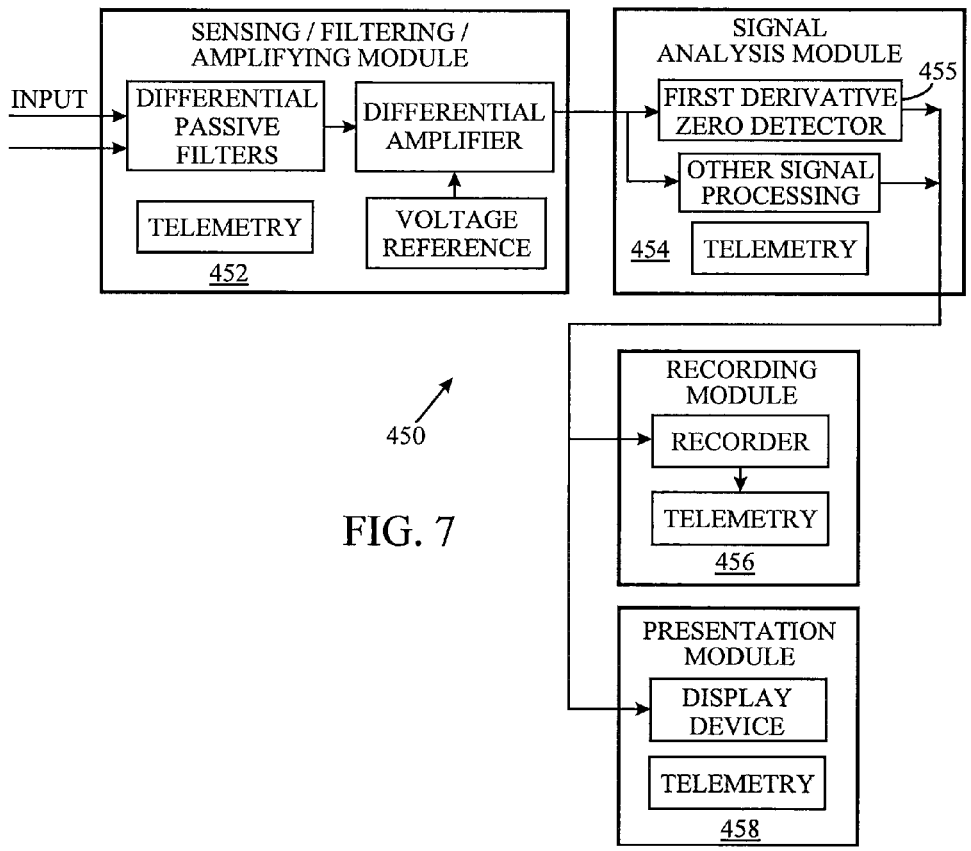
FIG. 7 is a block diagram of an implantable apparatus connected to a signal analysis module and a signal presentation module or a signal recording module.

Referring now to FIG. 7, a medical apparatus 450 comprises a sensing, filtering, and amplification module 452 connected to a signal analysis module 454, which in turn is connected to a recording module 456 and/or a signal presentation module 458. The illustrated configuration is applicable to both the implanted and external medical apparatus. For an implanted apparatus, modules 452, 454, and 456 are implanted within the patient, and module 458 is external. With an external apparatus, all the modules 452, 454, 456, 458 are external to the patient.

The sensing, filtering, and amplification module 452 can comprise version 100 in FIG. 4, version 400 in FIG. 6, or another like module including at least one implanted electrode pair disposed at a first set of locations to sense biological signals. Each electrode pair can be connected to a pair of insulated conductors that are in turn connected to an instrumentation amplifier via a passive network of filters. The amplifier amplifies the filtered biological signal from each of the electrode pairs to provide an amplified differential signal from the first set of locations. The amplifier has an internal voltage reference. Additionally, an energy source powers the apparatus without being connected to mains or an isolation transformer of medical equipment. The sensing, filtering, and amplification module 452 senses a biological signal, filters the sensed biological signal, and amplifies the filtered biological signal. The output of module 452 is an amplified differential signal.

Signal analysis module 454 receives the amplified differential signal from module 452. Signal analysis module 454 is configured to analyze the amplified differential signal to determine at least one physiological parameter of the biological signal sensed by module 452. For example, in a cardiac application of the apparatus, the parameter obtained may be heart rate. In general, the parameter extracted from the analysis module may be used to provide a-therapy (e.g., stimulation) to a patient. The signal analysis module may include a first derivative zero detector 455 to identify signal transitions. Detection of these zeroes provides a signal transition detector that is not subject to DC drift in the signal, is not subject to signal amplitude variations, does not lose signals with the usual filtering processes, that lends itself more amenably to robust feature detection, and that allows for reproduction of the original signal but without the DC component. Additional signal processing algorithms for detection and identification of biological signals may be used as part of the signal analysis module.

The recording module 456 can be connected to signal analysis module 454 to record the amplified differential signal and/or the at least one physiological parameter. The recording module 456 can be configured to communicate (for example, wirelessly via remote telemetry in the implanted context) to present saved and/or live data to a further module (not shown).

Additionally, presentation module 458 can be configured to receive the amplified differential signal and/or the at least one physiological parameter. The presentation module can display amplified signals and physiological parameters associated with the sensed biological signal. The presentation module may be accessed remotely via telemetry at a readout station (e.g., a doctor's office). Alternatively, the signal presentation module may provide a print out of a recording of the signal. In other alternatives, recorded signal may be stored in an electronic form for a later retrieval. The presentation module is located outside the body and in the internal context, can be configured to wirelessly communicate with signal analysis module 454 and/or module 452. Furthermore in the internal context, the presentation module 458 may be configured to wirelessly communicate with the recording module 456, which can be configured to transmit saved data to the presentation module 458.

An energy source for any of modules 452, 454, 456, and 458 can be a battery, an infrared source or a radio frequency source. The energy source is not connected to the mains or via an isolation transformer of medical equipment. This is to avoid connecting to any external grounding as mentioned earlier to avoid introduction of noise.

In summary, embodiments include leads that minimize EMI noise, passive filtering prior to signal amplification with a relatively high frequency, high pass filter with a cut-off frequency in the range of 20 to 70 Hz combined with a relatively high low pass filter with the cut-off frequency above 300 Hz, an amplifier with an internal voltage reference, and avoidance of connecting the energy source to an external ground. Embodiments also include a first derivative zero detector 455.

In one embodiment, at least a pair of electrodes may be located inside a blood vessel and sense signals from various tissue locations. In another embodiment, such as in the case of most nerve stimulators, the electrode location may be extravascular. In another embodiment, the electrode pair is implanted under the skin for detecting biological rhythms. In another embodiment, the electrode pair may be part of sensing pressure in the heart. In another embodiment, the electrode pair may be located on the outside of the patient. In general, the invention is applicable to signal amplification beyond nerve and cardiac applications where physical parameters are converted to electrical signals and could be affected by noise. Thus, the invention is applicable for sensing applications of all physiologic data including intravascular, extravascular, transvascular, and external muscle and nerve signals. The applicability of the invention further includes systems which are temporary and are both in the body and extend out of the body, such as temporary pacing leads.

The foregoing description was primarily directed to preferred embodiments of the invention. Although some attention was given to alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. An apparatus for sensing biological signals from an animal, the apparatus comprising:
   at least one set of electrodes that is adapted to be placed in contact with tissue of the animal at a set of locations to sense biological signals;

a set of insulated conductors connected to the at least one set of electrodes, the set of insulated conductors formed in a configuration adapted to be substantially immune to electromagnetic interference;

a network of filters connected to the set of insulated conductors and configured to filter the biological signals and thereby produce filtered biological signals;

an amplifier connected to the network of filters and having an internal voltage reference, the amplifier configured to amplify the filtered biological signals to provide an amplified differential signal, wherein the internal voltage reference also is connected to a node in the network of filters;

an energy source for powering at least the amplifier and configured to be free of all ground connections external to the apparatus; and a signal analysis module configured to receive and analyze the amplified differential signal to determine at least one physiological parameter of the animal.

2. The apparatus as recited in claim 1 further comprising at least one of a signal presentation module configured to display the amplified differential signal and a recording module to at least one of present and record the amplified differential signal.

3. The apparatus as recited in claim 1 wherein the set of locations of the at least one implantable electrode pair is on an external surface of the animal.

4. The apparatus as recited in claim 1 wherein the at least one physiological parameter is a heart rate of the animal.

5. The apparatus as recited in claim 1 wherein the network of filters comprises at least one high pass filter and at least one low pass filter.

6. The apparatus as recited in claim 5 wherein the at least one high pass filter is a single order filter.

7. The apparatus as recited in claim 5 wherein each of the at least one high pass filter and the at least one low pass filter is a passive filter comprising at least one capacitor and at least one resistor.

8. The apparatus as recited in claim 1 wherein the set of insulated conductors comprises multiple electrical conductors extending in parallel and spaced apart less than 3 mm.

9. The apparatus as recited in claim 1 wherein the signal analysis module comprises a first derivative zero detector.

10. The apparatus as recited in claim 1 wherein the network of filters comprises a low pass filter connected to the set of insulated conductors and including the node to which the internal voltage reference is connected.

11. The apparatus as recited in claim 10 wherein the low pass filter comprises a first element connected between the node and one conductor in the set of insulated conductors; and a second element connected between the node and another conductor in the set of insulated conductors.

12. An apparatus for sensing biological signals from an animal, the apparatus comprising:

an electrode pair adapted for implantation in the animal at intravascular locations to sense biological signals;

a pair of insulated conductors connected to the at least one electrode pair;

a passive network of filters connected to the pair of insulated conductors and configured to filter the biological signals and thereby produce filtered biological signals;

an instrumentation amplifier connected to the passive network of filters and having an internal voltage reference, the instrumentation amplifier being configured to amplify the filtered biological signals to produce an amplified signal, wherein the internal voltage reference also is connected to a node in the passive network of filters; and an energy source powering the apparatus and being isolated from all ground connections to the animal and external to the animal; and a signal analysis module configured to analyze the amplified signal.

13. The apparatus as recited in claim 12 wherein the passive network of filters comprises a low pass filter, a high pass filter, and a noise filter.

14. The apparatus as recited in claim 12 wherein the signal analysis module contains at least one first derivative zero detector.

15. The apparatus as recited in claim 12 wherein the passive network of filters comprises a low pass filter that includes the node to which the internal voltage reference is connected.

16. The apparatus as recited in claim 15 wherein the low pass filter comprises a first element connected between the node and one of the pair of insulated conductors; and a second element connected between the node and another one of the pair of insulated conductors.

17. An apparatus for sensing biological signals from an animal, the apparatus comprising:

at least one electrode pair disposed at a first set of locations to sense biological signals;

a pair of insulated conductors connected to the at least one electrode pair, the pair of insulated conductors being closely spaced to minimize sensitivity to electromagnetic interference;

an internal reference module configured to provide an internal reference voltage;

a filter network connected to the pair of insulated conductors and configured to provide a filtered biological signal, the filter network comprising at least one high pass filter and at least one low pass filter, the high pass filter configured to provide AC coupling and the low pass filter configured to provide noise rejection, wherein the internal reference voltage is applied to a node of one of the at least one low pass filter;

an instrumentation amplifier connected to the filter network, the instrumentation amplifier configured to receive the internal reference voltage, and to amplify the filtered biological signal to provide an amplified biological signal;

an energy source powering the apparatus, the energy source configured to be free of a wired connection to an energy supply external to the animal; and a signal analysis module configured to analyze the amplified differential signal to extract at least one physiological parameter of the animal;

wherein the apparatus is substantially free of all wired ground connections to a ground external to the apparatus.

18. The apparatus as recited in claim 17 wherein the signal analysis module contains at least one first derivative zero detector.

19. The apparatus as recited in claim 17 wherein the first set of locations of the at least one electrode pair is on an external surface of the animal.

20. The apparatus as recited in claim 17 wherein the first set of locations of the at least one electrode pair is inside the animal.

* * * * *